United States Patent

Furuichi et al.

[11] Patent Number: 5,972,611
[45] Date of Patent: *Oct. 26, 1999

[54] HYBRIDIZATION CARRIER AND A PROCESS FOR PREPARING THE SAME

[75] Inventors: Yasuhiro Furuichi, Kamakura; Mikio Hikata; Keiko Kuribayashi, both of Yokohama, all of Japan

[73] Assignee: JSR Corporation, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/964,448

[22] Filed: Nov. 4, 1997

Related U.S. Application Data

[63] Continuation of application No. 08/662,830, Jun. 12, 1996, abandoned, which is a continuation of application No. 08/437,910, May 10, 1995, abandoned, which is a continuation of application No. 08/003,904, Jan. 13, 1993, abandoned, which is a continuation of application No. 07/888,409, May 21, 1992, abandoned, which is a continuation of application No. 07/674,284, Mar. 21, 1991, abandoned, which is a continuation of application No. 07/288,601, Dec. 22, 1988, abandoned.

[30] Foreign Application Priority Data

Dec. 25, 1987 [JP] Japan .................................. 62-329402

[51] Int. Cl.$^6$ .............................. C12Q 1/68; C12P 19/34; C07H 21/02; C07H 21/04
[52] U.S. Cl. ........................ 435/6; 435/91.1; 536/24.2; 536/24.3; 536/24.33; 935/77; 935/78
[58] Field of Search .................... 435/6, 91.1; 536/22.1, 536/24.2, 24.3, 24.33; 935/77, 78

[56] References Cited

U.S. PATENT DOCUMENTS

| | | | |
|---|---|---|---|
| 3,837,931 | 9/1974 | Hager | 435/6 |
| 4,569,794 | 2/1986 | Smith et al. | 435/6 |
| 4,734,363 | 3/1988 | Dattagupta et al. | 435/6 |
| 4,739,044 | 4/1988 | Stabinsky | 435/6 |
| 4,783,336 | 11/1988 | Margel | 435/6 |
| 4,794,073 | 12/1988 | Dattagupta et al. | 435/6 |
| 4,797,355 | 1/1989 | Stabibsky | 435/6 |
| 4,806,546 | 2/1989 | Carrico et al. | 435/6 |
| 4,818,681 | 4/1989 | Dattagupta | 435/6 |

FOREIGN PATENT DOCUMENTS

| | | |
|---|---|---|
| 0 288 737 | 11/1988 | European Pat. Off. . |
| 2 567 523 | 7/1984 | France . |

OTHER PUBLICATIONS

Fiers, et al., European Patent Application 041 767 (1981).
Dattagupta et al., European Patent Application 184 056 (1986).
Bujard et al., European Patent Application 186 069 (1986).
Jolley et al., European Patent Application 200 113 (1986).
Fahrner, et al., Nuc. Acids Res. 8:5725–5737 (1980).
Ghosh et al., "Covalent attachment of oligonucleotides to solid supports", Nucleic Acids Research, vol. 15, No. 13, pp. 5353–5372 (1987).
Kremsky et al., "Immobilization of DNA via oligonucleotides containing an aldehyde or carboxylic acid group at the 5' terminus", Nucleic Acids Research, vol. 16, No. 7, pp. 2891–2909 (1987).

*Primary Examiner*—Stephanie Zitomer
*Attorney, Agent, or Firm*—Oblon, Spivak, McClelland, Maier & Neustadt, P.C.

[57] ABSTRACT

A hybridization carrier, containing a single-stranded polynucleotide having the formula:

$$5'\text{-}(dN)_n(dT)_m\text{-}3',$$

wherein N represents admine, guanine or cytosin; T represents thymine; n is an integer of 2 or larger; and m is an integer of 5 or larger;

the polynucleotide being immobilized by an amide bond on a surface of an organic polymers particle having a diameter of from about 0.05 $\mu$m to about 5 $\mu$m;

the polynucleotide being immobilized at the site of a nucleotide sequence consisting of 2 or more polynucleotide which contain a primary amino residue in the polynucleotide; and the amide bond having been formed between the primary amino residue and a carboxyl residue on the surface of the organic polymer particle.

21 Claims, 1 Drawing Sheet

HYBRIDIZATION CARRIER AND A PROCESS FOR PREPARING THE SAME

This is a continuation of application Ser. No. 08/662,830, filed Jun. 14, 1996, now abandoned, which is a continuation of Ser. No. 08/437,910, filed May 10, 1995, now abandoned, which is a continuation of Ser. No. 08/003,904, filed Jan. 13, 1993, now abandoned, which is a continuation of Ser. No. 07/888,409, filed May 21, 1992, now abandoned, which is a continuation of Ser. No. 07/674,284, filed Mar. 21, 1991, now abandoned, which is a continuation of Ser. No. 07/288,601, filed Dec. 22, 1988, now abandoned.

TECHNICAL FIELD

This invention relates to a hybridization carrier which is useful for the detection, isolation, purification and cloning of nucleic acids, especially messenger RNA (mRNA) containing a polyadenylic acid sequence, and to a process for preparing the same.

BACKGROUND OF THE INVENTION

A solid support with a nucleic acid immobilized on its surface is known as a useful material for the techniques of detecting, isolating and purifying nucleic acids containing the desired specific base sequence. This technique is a method developed by scientists in the field of recombinant DNA technology, the application of which is based on the observation that DNA or RNA denatured to the single-stranded form can hybridize with other single-stranded nucleic acids containing substantially complementary base sequences through hydrogen bonding between the bases under suitable conditions.

As a method of immobilizing a single-stranded nucleic acid on the surface of solid support, a method was developed which comprised bringing a solid support composed of materials having high affinities for nucleic acids such as nitrocellulose or nylon membranes into contact with a nucleic acid, trapping the nucleic acid on the support and then baking or UV irradiating the resulting support to strengthen the immobilization. This method, however, is undesirable because nucleic acids that lack the desired specific base sequence in a sample and nucleic acid detection probes are also likely to be trapped on the surface of the support because of the high nonspecific affinity of the solid support for nucleic acids. To prevent such nonspecific binding, this method requires very tedius operations of coating the surface of the support with a polymeric substance foreign to the desired specific base sequence, and repeated washing of the support after a hybrid is formed.

To overcome the problems described above, various nucleic acid immobilization supports and their manufacturing processes have been proposed. Among these is a support that immobilizes a nucleic acid through a carbon chain having 4 to 20 carbon atoms (part of the carbon atoms may be substituted with a heteroatom such as O, N, S or the like and this chain is referred to as "arm") between a nucleotide sequence-part constituting the nucleic acid and a support. This nucleic acid immobilization support is manufactured by previously activating a given part of a base in a nucleotide to produce an immobilization site and then reacting the activated part with a reactive residue provided for the support as an "arm", to form a covalent bond (Japanese Patent Application Kokai No. 130305/1986). A method of ligating a nucleic acid to a support using an enzymatic reaction has also been described (Japanese Patent Application Kokai No. 246201/1986).

However, the method described in the official gazette of Japanese Patent Application Kokai No. 130305/1986 requires the protection of other reactive residues in a nucleic acid by protective residues, at the time a given part of a base is activated. In addition, it is necessary to completely eliminate the protective residues after immobilizing the nucleic acid on the support. During the elimination of the protective residues, several changes of reaction solvent and recovery and purification of the reaction product are required. Furthermore, the reaction can be a very lengthy operation, sometimes taking several hours to several days to carry out.

The method described in the official gazette of Japanese Patent Application Kokai No. 24601/1986 requires the ligation of a nucleic acid in a given direction to increase the effective amount of immobilized nucleotide or oligonucleotide. Thus remarkably tedious operations are also required for this method. In addition, large amounts of an expensive enzyme are required, making this method economically disadvantageous.

Consequently, the above methods are impractical for daily use.

DESCRIPTION OF THE INVENTION

An object of the present invention is to provide a hybridization carrier on which a nucleic acid can be immobilized simply and efficiently with minimal nonspecific trapping. A further object of the invention is to enable the highly accurate detection, isolation, purification and cloning of specific nucleic acids in a sample such as a cell or tissue extract, and to provide a method for preparing the same.

To avoid the foregoing problems of the prior art, the present invention provides a hybridization carrier in which a single-stranded polynucleotide represented by the formula $$5'\text{-}(dN)_n(dT)_m\text{-}3',$$

wherein N represents adenine, guanine or cytosine; T represents thymine: n is an integer of 2 or larger and m is an integer of 5 or larger, is immobilized by means of a peptide bond on a non-porous surface of an organic polymer particle having a diameter of about 0.05–5 μm.

The organic polymer particles used as carriers in the present invention (hereinafter referred to as "polymer particles") are water-insoluble organic polymer substances obtained by polymerizing one or more vinyl monomers composed of aromatic compounds, esters or amides of α,β-unsaturated carboxylic acids, α,β-unsaturated nitrile compounds. halogenic vinyl compounds, conjugated-diene compounds and lower fatty acid vinyl esters. Examples, of such monomers include but are not limited to styrene, chlorostyrene, chloromethylstyrene, α-methyl-styrene, divinylbenzene, sodium styrene sulfonate, methacrylic acid, methyl methacrylate, ethyl methacrylate, n-butyl methacrylate, 2-hydroxyethyl methacrylate, polyoxyethylene methacrylate, glycidyl methacrylate, ethylene glycol-dimethacrylic acid ester, tribromophenyl methacrylate, methacrylnitrile, methacrolein, methacrylamide, methylenebis-methacrylamide, butadiene, isoprene, vinyl acetate, vinyl pyridine, N-vinyl pyrrolidone, vinyl chloride and vinyl bromide.

The polymer particles can be manufactured using well-known methods such as emulsion polymerization, suspension polymerization, solution precipitation polymerization, etc. They can be also obtained by dispersing an organic polymer solution in a nonsolvent to carry out the crosslinking or by dispersing a solvent. Other methods for making the polymer particles will be apparent to those skilled in the art. The polymer particles can also contain other materials, e.g., magnetic powder or the like as desired.

The surface of the polymer particles used in the present invention must be non-porous. As used herein, "non-porous" means that the longest dimensions of pores on the surfaces of the particles are less than 100 A (angstrom units).

If the surfaces of the polymer particles are instead porous, i.e., if they contain pores having longest dimensions of 100 A or more, the sensitivity and accuracy of the hybridization may be reduced due to entrapment of labeled probes used in the nucleic acid detection method, etc. Furthermore, substances other than the intended isolation target may become trapped inside porous polymer particles when such particles are used to isolate or purify a nucleic acid, thereby reducing the isolation efficiency or the degree of purification.

Although the surfaces of the polymer particles must be non-porous, the interiors of the particles may contain larger closed cells and the like.

The size of the polymer particles used in the present invention is about 0.05 to about 5 $\mu$m, preferably about 0.2 to about 4 $\mu$m in diameter. Such particles remain in suspension for prolonged periods of time, but can readily be sedimented by centrifugation. Particles smaller than about 0.05 $\mu$m require a long time to centrifuge from a sample solution following hybridization. Particles larger than about 5 $\mu$m may sediment in a sample solution before hybridization is complete.

Since the polymer particles used in the present invention are used in aqueous solutions, they should be water-insoluble and non-swelling.

A single-stranded polynucleotide carried by the carriers of the present invention is a single-stranded deoxyribonucleic acid represented by the formula

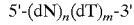

$5'-(dN)_n(dT)_m-3'$ as described above. This polynucleotide can be obtained either by chemical synthesis as described below or by artificial modifications such as the addition of one or more nucleotides to a natural nucleic acid.

This single-stranded polynucleotide is bonded to a polymer particle by means of a peptide bond, at the site of a nucleotide sequence in the single-stranded polynucleotide consisting of 2 or more, generally 2 to 15, nucleotides with contain primary amino residues. When the number of nucleotide containing primary amino residues is below 2, the immobilization ratio of a single-stranded polynucleotide on a polymer particle will be undesirably low.

Nucleotides containing primary amino residues include, e.g., deoxyadenylic acid (dA), deoxycytidylic acid (dC) and deoxyguanylic acid (dG). Among these, dA and dC are preferable in that they are more reactive in condensation with a carboxyl residue on the surface of a polymer particle. The amino residue-containing nucleotide sequence may be composed of 1 kind of nucleotide or of 2 or more nucleotides. However, to avoid a base sequence accidentally becoming complementary to a base sequence other than a specific base sequence in a nucleic acid that is to be hybridized, it is preferred that the amino residue-containing nucleotide sequence be composed of 1 kind of nucleotide, particularly dA or dC.

If a single-stranded polynucleotide used in the preparation of the present carriers contains no amino residue-containing nucleotide sequence, such a sequence must be introduced into the molecule prior to use. If the single-stranded polynucleotide is produced by chemical synthesis using, for example, a DNA synthesizer, the amino residue-containing nucleotide sequence can be introduced at the desired position in the polynucleotide during the synthetic process. The sequence can be also introduced at the terminus of the polynucleotide, using terminal deoxytransferase. Alternatively, the sequence can be introduced by ligating the polynucleotide with an oligonucleotide consisting of amino residue-containing nucleotide sequences, using T4 DNA ligase. These methods are well known and are described, e.g., in Maniatis et al., "Molecular Cloning", Cold Spring Harbor Laboratories, 1982, which is hereby incorporated by reference.

A single-stranded polynucleotide carried by the carriers of the present invention can hybridize with other nucleic acids which will serve as a target of detection, purification, isolation, etc. The carrier of the present invention is preferable for hybridization, since a base sequence complementary to a poly (A) sequence portion of a nucleic acid to be hybridized with exists in a portion of a free site of the nucleotide.

Particularly, a linear single-stranded polynucleotide is immobilized on a polymer particle on the side of 5'-terminal and a base sequence complementary to a specific base sequence exists on the side of free 3'-terminal, which enables the elongation reaction of a nucleic acid by a nucleic acid-synthesizing enzyme in which the immobilized single-stranded polynucleotide acts as a primer. Thus the linear single-stranded polynucleotide can be used for the synthesis of cloned DNA or for the detection of a specific base sequence based on the incorporation of labeled nucleotide on a polymer particle.

A carrier according to the present invention can be prepared, for example, by reacting a polymer particle having a non-porous surface, a carboxyl residue and a particle diameter size of 0.05 to 5 $\mu$m, with the single-stranded polynucleotide described above, in the presence of a condensing agent.

The polymer particles used as starting materials in this method must have carboxyl residues that can participate in the formation of peptide bonds on their surfaces. If polymer particles that are to be used have no carboxyl residues on their surfaces, such residues must first be introduced onto the surfaces of the particles. The density of carboxyl residues on the surface of the polymer particles should preferably be at least 1, more preferably 3 or more and much more preferably 5 or more per am of surface area.

Polymer particles having carboxyl residues on their surfaces which are suitable for use in this invention include, for example, commercially available particles marketed under trade names such as Immutex SSM-60, SSM-58, SSM-57, G0303, G0302, G0301, G0201, G0202, G0501, L0101 and L0102; and Immutex DRB-F1, DRB-F2, DRB-F3; etc. (all are trade names of carboxylated polystyrene particles manufactured by Japan synthetic Rubber Co., Ltd.). Carboxyl residues can be introduced onto the surfaces of polymer particles lacking such residues, using various well-known methods. The physicochemical properties of some of the particles mentioned above are as follows:

| Trade Name | Mean Diameter ($\mu$m) | Density of Surface Charge (m eg COO—/g) | Density of Surface Carboxyl Residue (—COOH/nm$^2$) |
|---|---|---|---|
| Immutex G0202 | 0.26 | 0.1 | 3 |
| Immutex G0201 | 0.30 | 0.1 | 3 |

| Trade Name | Mean Diameter (μm) | Density of Surface Charge (m eg COO—/g) | Density of Surface Carboxyl Residue (—COOH/nm$^2$) |
|---|---|---|---|
| Immutex G0301 | 0.31 | 0.1 | 2 |
| Immutex G0302 | 0.37 | 0.1 | 5 |
| Immutex G0303 | 0.37 | 0.1 | 5 |
| Immutex G0501 | 0.58 | 0.08 | 5 |
| Immutex L0101 | 1.1 | 0.09 | 10 |
| Immutex L0102 | 1.2 | 0.03 | 4 |
| Immutex SSM-60 | 0.36 | — | 9 |

Preferred condensing agents which can be used in this invention include, water-soluble carbodiimides like 1-ethyl-3-(N,N'-dimethylamino)propylcarbodiimide, Woodward's reagent K, N-ethoxycarbonyl-2-ethoxy-1,2-dihydroquinoline (EEDQ), etc. However, oil-soluble condensing agents can be also used. These condensing agents are generally used in the amount of 1 to 20 moles, preferably in the amount of 2 to 10 moles per equivalent of carboxyl residues on the surfaces of the polymer particles used.

The condensation reaction can be carried out, for example, by putting polymer particles having carboxyl residues on their surfaces and a single-stranded polynucleotide containing an amino residue-containing nucleotide sequence into a reactor of suitable volume and then adding the foregoing condensing agent thereto. The amount of polymer particle to be used is generally 0.5 to 500 g, preferably 5 to 50 g per mmol of single-stranded polynucleotide containing amino residue-containing nucleotide sequence. It is generally sufficient to carry out the reaction in an aqueous medium of about pH 3 to 11 at about 4 to 70° C. for 5 minutes to overnight.

The present carrier and the preparation method described above can be used for the detection of nucleic acids using a sandwich method and a competitive method.

In the sandwich method, two different and nonoverlapping specific base sequences, one of which is a poly (A) sequence, are first selected from the base sequences contained in a nucleic acid that is to be detected in a sample. The carrier of the present invention carries a polynucleotide having a sequence complementary to poly (A). A labeled nucleic acid probe is prepared by labeling a nucleic acid that is complementary to the above specific base sequence at a point other than the poly (A) sequence, with an appropriate label. When the carrier and the labeled nucleic acid probe are subjected to hybridization with a nucleic acid in a sample under conditions in which specific hybridization occurs, the nucleic acid of the carrier and the labeled nucleic acid probe are bonded in the form of a sandwich with the nucleic acid from the sample, if the nucleic acid in the sample contains a poly (A) sequence. Then, the labeled nucleic acid bonded to the carrier is detected by an appropriate method.

In the competitive method, a single-stranded nucleic acid containing a base sequence complementary to a poly (A) sequence of a mRNA to be detected in a sample is first bonded to a polymer particle to prepare a carrier of the present invention. A nucleic acid containing a poly (A) sequence substantially equal to that of a nucleic acid to be detected in the specimen is labeled to prepare a probe. Then, the foregoing carrier, the specimen and the probe are mixed and subjected to the hybridization reaction where, if a nucleic acid containing a specific base sequence to be detected is present in the sample, the nucleic acid competes with the probe for hybridization with the single-stranded nucleic acid bonded to the carrier. If such a nucleic acid is not present in the sample, only the probe will hybridize with the single-stranded nucleic acid on the carrier. The amount of probe hybridized with the single-stranded nucleic acid on the carrier decreases in direct proportion to the amount of nucleic acid to be detected in the sample.

In the sandwich method and the competitive method described above, a specimen containing nucleic acids, labeled nucleic acid probes and a buffer suitable for the hybrid formation are added to nucleic acid-bonded polymer particles and allowed to stand for about 2 hours at a temperature at which specific hybridization occurs (e.g., 37° C.; see Maniatis et al., supra), thereby forming hybrids. Then, the excess labeled nucleic acid probes are removed by centrifugation or the like and the labels bonded to the carriers are detected.

A probe used in the detection of nucleic acids described above consists of a single-stranded nucleic acid as a direct target of the detection labeled with an easily detectable label. A label used in this invention is a substance which can be easily detected as a tracer such as an enzymatically active residue (e.g., a peroxidase), fluor, chromophor, luminophor, specifically bondable ligand, heavy metal and radioactive isotope. Because of the label, a labeled probe trapped on a carrier due to hybridization can easily be detected.

The above-mentioned methods can be used to detect pathogens such as bacteria, viruses, etc., and for the screening of antibiotics and antiviral agents, the diagnosis of hereditary disorders and the detection of cancer cells.

The present carrier can also be used for the isolation of mRNA containing poly (A) sequences.

The isolation of nucleic acids is carried out by first immobilizing a single-stranded nucleic acid containing a base sequence complementary to a poly (A) sequence in a mRNA sample on a polymer particle to form the present carrier, then making the carrier hybridize with a mRNA containing a poly (A) sequence in the foregoing mRNA sample and isolating the mRNA hybridized with the carrier.

The hybridized nucleic acid can be isolated by removing undesired nucleic acids and other materials, e.g., by centrifugation or filtration, and then subjecting the hybrid products to a heat treatment or to a treatment with alkali, formamide or urea to break the hydrogen bonds between the nucleic acids in the hybrid. Then, the dissociated nucleic acid containing the desired specific base sequence can be recovered.

Such isolation of nucleic acids is useful for obtaining mRNA which encodes proteins useful for human beings, animals, plants or microorganisms from samples such as crude extracts of cells and tissues.

The particles of the present invention are superior to oligo (dT) cellulose for the isolation of mRNA. Such cellulose must generally be used in a column and is not readily applicable to small samples. In contrast, the particles of this invention can be used for multiple small samples such as test tube samples. Furthermore, these particles are mechanically stable, unlike cellulose which in use can shed troublesome fine fiber fragments.

The specific conditions such as a buffer, temperature, reaction time, etc. suitable for the specific hybridizations described above are well known to those skilled in the art.

The present carrier can also be used for the cloning of isolated nucleic acids, particularly RNA. A single-stranded nucleic acid containing a sequence complementary to a part of a sequence that is to be cloned at its 3'-portion (hereinafter referred to as an "immobilized nucleic acid") is immobilized on a particle to form the present carrier. The carrier is then hybridized with the nucleic acid to be cloned in a sample (hereinafter referred to as "target nucleic acid"). A reverse transcriptase is used in a process in which the target nucleic acid and the immobilized nucleic acid serve respectively as a template and a primer. In this way, a DNA containing a sequence complementary to the target nucleic acid (hereinafter referred to as a "primary strand of cloned DNA") can be synthesized.

By applying the methods of Okayama and Berg (H. Okayama and P. Berg; Molecular and Cellular Biology, 2, 161–170, 1982), Gubler and Hoffmann (U. Gubler and G. J. Hoffmann:

Gene, 25, 263–269, 1983) and Williams (Williams, J. G.: "Genetic Engineering", vol. 1, p. 1–59, Academic Press, London and New York, 1981), a sequence complementary to the primary strand of a cloned DNA, that is a DNA containing a s sequence corresponding to that of the target nucleic acid (hereinafter referred to as "secondary strand of cloned DNA") can synthesized.

By inserting a recognition sequence for a restriction enzyme between a sequence consisting of 2 or more nucleotides containing primary amino residues in the immobilized nucleic acid and a sequence complementary to a part of the target nucleic acid in 3'-portion also in the immobilized nucleic acid, the cloned DNA can be excised from the carrier using the restriction enzyme after synthesis of the secondary stand of the cloned DNA is complete. The cloned DNA can thus be recovered.

After synthesizing the primary strand of a cloned DNA by the use of an immobilized nucleic acid containing a recognition sequence for the restriction enzyme, oligo(dA), oligo (dT), oligo(dc) or oligo(dG) is added to the 5'-terminal of the cloned DNA using the addition reaction. Then the target nucleic acid is eliminated by decomposition or denaturation to form a hybrid between a single-stranded nucleic acid containing not only a sequence complementary to the added oligonucleotide (addition sequence) in its 3'-portion but also a recognition sequence for the restriction enzyme and the tailed site of the primary strand of a cloned DNA.

After synthesizing the secondary strand of a cloned DNA by using an enzyme such as DNA polymerase, with the single-stranded nucleic acid complementary to the addition sequence and the primary strand of a cloned DNA serving respectively as a primer and a template, a restriction enzyme can be used to excise a cloned DNA having a recognition site for a restriction enzyme at both its 5'- and 3' termini from the carrier to facilitate recovery of the cloned DNA. The cloned DNA can then be incorporated into a plasmid having a similar recognition site for the restriction enzyme. In this method for synthesizing a cloned DNA, the single-stranded nucleic acid complementary to the tailed nucleic acid can be the present hybridization carrier immobilized on a polymer particle.

EXAMPLES

Figure 1:
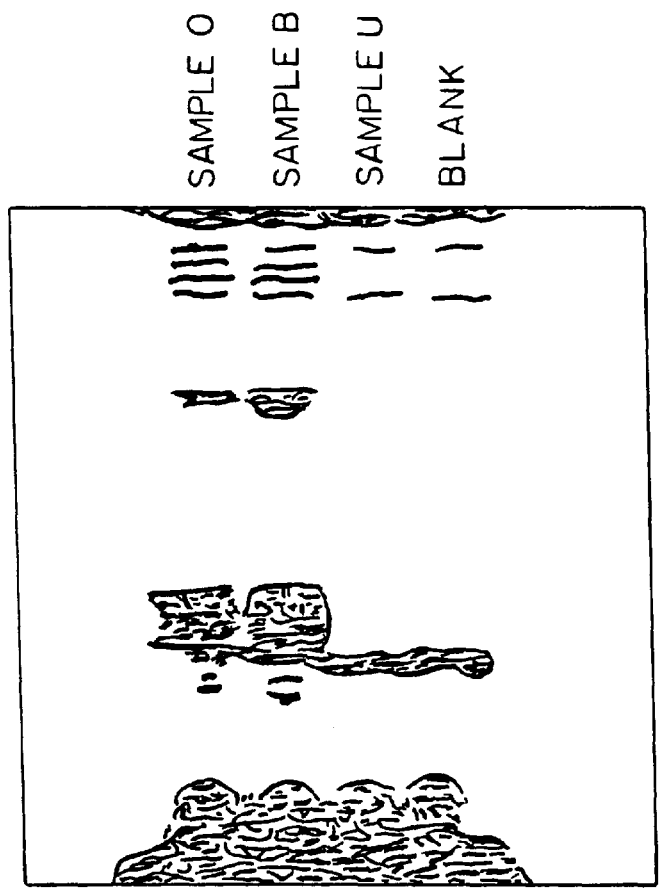
FIGS. 1 and 2 are autoradiograms obtained after subjecting the reaction solutions of globin protein synthesized in Example 4 to electrophoresis and drying.

The present invention can be more readily understood by reference to the following, nonlimiting examples.

Example 1
(1) Preparation of Polynucleotide 5'-(dC)$_n$D(dT)$_{30}$-3' (n=0, 1, 3, 7 or 10)

Five kinds of polynucleotides whose nucleotide sequences are represented by 5'-(dC)$_n$(dT)$_{30}$-3' (n=0, 1, 3, 7 or 10). [wherein 5'- on the left end and 3'- on the right end respectively stand for 5'-terminal and 3'-terminal (which will stand for the same meanings hereinafter)] were synthesized with a DNA synthesizer (Model 381A: Applied Bio System, Inc.) using the solid phase, β-cyanoethyl method. The excision and collection of the synthesized polynucleotide from the solid phase were carried out according to instructions in the manual for the synthesizer.

Each of the polynucleotides obtained was dissolved in 250 μl of TNE buffer [10 mM Tris-HCl, pH 7.5, 100 mM sodium chloride and 1 mM ethylenediaminetetraacetic acid (EDTA)], and subjected to gel filtration using a Sephadex® G-50 column (Pharmacia Fine Chemicals, Inc.) swollen with the TNE buffer. The eluates from the gel filtration were fractioned into 0.5 ml portions and collected successively, and the absorbance of each fraction at 260 nm was measured.

The polynucleotides in the collected fractions were purified by precipitation with ethanol. Each purified polynucleotide was dissolved in 500 μl of sterile water, and the absorbance at 260 nm was measured to determine the amount of each polynucleotide.

As a result of the above procedures, about 1 mg each of the polynucleotides mentioned above was obtained.

(2) Labeling with $^{32}$P

Each of the polynucleotides obtained in (1) was labeled with $^{32}$P as follows:

1 μl of one of the polynucleotide solutions (containing 2 μg of polynucleotide), 1 μl (8 units of enzymatic activity; enzyme units used here and below were as defined by the manufacturer) of polynucleotide kinase (Boehringer Mannheim, Inc.), 5 μl (50 μCi) of γ-$^{32}$P-deoxyadenosine triphosphate, 5 μl of 10-fold concentrated 5'-terminal phosphorylation buffer (0.5 M Tris-HCl, pH 7.6, 0.1 M MgCl$_2$, 50 mM dithiothreitol, 1 mM spermidine, 1 mM EDTA) and 38 μl of sterile water were added to a 1.5 ml microcentrifuge tube, mixed and incubated at 37° C. for 30 minutes.

After removing the polynucleotide kinase from the reaction solution using the phenol extraction method ("Molecular Cloning", Cold Spring Harbor Laboratories, p. 458, 1982), the reaction solution was subjected to gel filtration using a 1 ml Sephadex® G-50 column (Pharmacia Fine Chemicals, Inc.) swollen with TNE buffer.

The eluate from the column was fractioned into 100-μl portions and collected. The radioactivity of each fraction was measured by Cerenkov's counting method [Braunsberg et al., Anal. Biochem. 10:86 (1965)]. As a result, 200 μl each of TNE buffers containing the polynucleotides of 5'-(dC)$_n$(dT)$_{30}$-3' (wherein n=0, 1, 3, 7 or 10) labeled with $^{32}$P was obtained. These solutions each contained about 400,000 cpm/μl radioactivity.

(3) Immobilization On Polymer Particles Having Carboxylated Surfaces

500 μl of a 0.0001 N HCl suspension containing it (w/v) Immutex SSM-60 (Japan Synthetic Rubber, Co., Ltd.; a polymer particle of 0.36 μm diameter whose surface is carboxylated to have 9 carboxyl residues per nm$^2$ of surface area), 1 nmol of a polynucleotide having a nucleotide sequence of 5'-(dC)$_n$(dT)$_{30}$-3' (wherein n=0, 1, 3, 7 or 10), 500 μl of 0.0001 N HCl solution containing 0.5% (w/v) 1-ethyl-3-(N,N'-dimethylamino)propylcarbodiimide and 400,000 cpm of a $^{32}$P-labeled polynucleotide (having the same dC number as the non-labeled polynucleotide) were added into a 1.5-ml microcentrifuge tube and mixed overnight at 50° C., whereby the $^{32}$P-labeled polynucleotide was bonded to the polymer particle by a peptide bond.

The resulting product was centrifuged at 10,000 rpm for 5 minutes to recover the hybridization carrier as a precipitate. The hybridization carrier was washed by repeating the operations of adding thereto 1 ml of binding buffer (10 mM Tris-HCl buffer, pH 7.5, 500 mM sodium chloride, 0.1% (w/v) sodium dodecylsulfate and 1 mM EDTA to redisperse the same, then centrifuging the dispersion at 15,000 rpm for 5 minutes to recover the hybridization carrier.

The remaining radioactivity on the isolated hybridization carrier was measured according to Cerenkov's counting method. The immobilization ratio was obtained by dividing the remaining radioactivity value by the count number of the added $^{32}$P-labeled oligonucleotide (400,000 cpm). The results are given in Table 1.

TABLE 1

| Number of n in $(dC)_n (dT)_{30}$ | Immobilization Ratio (%) |
|---|---|
| 0 | 9 |
| 1 | 52 |
| 3 | 72 |
| 7 | 89 |
| 10 | 93 |

Example 2
Determination of Polyadenylic Acid Sequences Contained In Vaccinia Virus mRNA
(1) Preparation of Hybridization Carrier A polynucleotide of 5'-(dC)$_{10}$(dT)$_{30}$-3' having a base sequence of 5'-CCCCCCCCCCTTTTTTTTTTTTTTTTTT-TTTTTTTTTTTT-3' was synthesized in a DNA synthesizer. The (dT)$_{30}$ sequence on the side of the 3'-terminal of this polynucleotide was complementary to a polyadenylic acid (hereinafter abbreviated as "poly(A)") sequence contained in a mRNA of vaccinia virus. The (dC)$_{10}$ sequence on the side of the 5'-terminal was used for immobilization onto a polymer particle.

2.5 ml of a 0.0001 N HCl suspension containing 1% (w/v) surface-carboxylated polymer particle (Immutex SSM-60; Japan Synthetic Rubber Co., Ltd.), 2.5 ml of a 0.0001 N HCl solution containing 5 mg/ml of 1-ethyl-3-(N,N'-dimethylamino)propylcarbodiimide, 100 µg of the above synthetic polynucleotide and 10,000 cpm of the above synthetic polynucleotide labeled with $^{32}$P in the same manner as in Example 1-(2) were mixed and reacted at 50° C. for 6 hours. After the reaction, a suspension of hybridization carrier was centrifuged at 3000 rpm for 15 minutes to recover the hybridsulfation carrier. The recovered hybridization carrier was washed by repeating the operations of suspension in 10 ml of 0.0001 N HCl and centrifugation. After thoroughly washing, the hybridization carrier was suspended in a solution consisting of 10 mM tris-HCl buffer (pH 7.5), 0.1 M sodium chloride, 1 mM EDTA (pH 7.5) and 0.1% (w/v) sodium dodecylsulfate to give a total volume of 5 ml. The thus-obtained 0.5% (w/v) suspension of hybridization carrier was preserved at 4° C.

The immobilization ratio of polynucleotide on the hybridization carrier was found to be 98%. (i.e., 98 µg of polynucleotide were immobilized on the polymer particle on the side of the 5'-terminal).

(2) Preparation of Poly(A)-containing Vaccinia Virus mRNA

Vaccinia virus was washed with a surfactant [0.5% (w/v) NP40] and recovered as a pellet by centrifugation. To this pellet were added 2000 µl of a solution containing 50 mM Tris-HCl buffer (pH 8.6), 7.5 mM magnesium chloride, 20 mM β-mercaptoethanol, 5 mM adenosine triphosphate, 5 mM cytidine triphosphate, 5 mM guanosine triphosphate, 5 mM uridine triphosphate, 0.5% NP40, 0.3 mM S-adenosylmethionine and RNase inhibitor. The mixture was incubated at 37° C. for 3 hours. Then, a supernatant obtained by centrifuging the reaction solution at 15,000 rpm for 10 minutes was extracted with phenol, and subjected to column chromatography using Sephadex® G-100 (Pharmacia Fine Chemicals, Inc.), thereby collecting untrapped fractions.

The collected fractions were applied to a column packed with oligo(dT)-cellulose to fractionate the same into mRNAs containing poly(A) sequences and those not containing poly(A) sequences, whereby 18 µg of mRNA containing poly(A) sequences and 10 µg of mRNA not containing poly(A) sequences were obtained.

(3) Determination of mRNA Containing Poly(A) Sequences
(3-1)

20 µl of the suspension of hybridization carrier prepared in (1) were added to a microcentrifuge tube with 1 ml of 100 mM Tris-HCl buffer (pH 8.3). The suspension was centrifuged at 10,000 rpm for 5 minutes to recover the hybridization carrier.

To this hybridization carrier were added 49 µl of a solution having the following composition:

100 mM Tris-HCl buffer (pH 8.3)

160 mM potassium chloride 20 mM β-mercaptoethanol 1 mM deoxyadenosine triphosphate 1 mM deoxyguanosine triphosphate 1 mM deoxythymidine triphosphate 0.1 mM deoxycytidine triphosphate 10 µCi α-$^{32}$P-deoxycytidine triphosphate 10 mM magnesium chloride 8 units of RNase inhibitor 10 ng, 1 ng, 0.1 ng or 0 ng quantities of the mRNA containing poly(A) sequence prepared in (2) which were previously subjected to heat treatment at 65° C. for 5 minutes and to rapid cooling on ice were added to the above solution, which was then incubated at 43° C. for 10 minutes to cause hybrid formation. Then, 1 µl (17 units) of reverse transcriptase (Life Science, Inc.) was added to the reaction solution, and incubation was continued at 43° C. for 15 minutes. Thereafter, 1 µl of 0.5 M EDTA (pH 8.0) was added to the incubated reaction solution, and the suspension was washed with a solution consisting of 10 mM Tris-HCl buffer (pH 8.0), 100 mM sodium chloride and 1 mM EDTA (pH 8.0) and filtered under suction through a 0.22-µm nitrocellulose membrane filter (GSWP 025, Millipore).

After washing, the membrane filter was dried and the radioactivity of the hybridization carrier on the membrane filter was measured in a liquid scintillation spectrometer.

(3-2)

The experiment was carried out by following the same procedure as described in the foregoing (3-1) except that mRNA not containing a poly(A) sequence prepared in (2) was used instead of mRNA containing a poly(A) sequence. The radioactivity of the hybridization carrier on the membrane filter was measured.

(3-3)

The results of the determination in (3-1) and (3-2) are given in Table 2.

TABLE 2

| | Radioactivity of Hybridization Carrier (cpm) | |
|---|---|---|
| | Type of mRNA | |
| Amount of mRNA added (ng) | mRNA containing poly(A) sequence | mRNA not containing poly(A) sequence |
| 10 | 43,230 | 73 |
| 1 | 5,995 | 108 |
| 0.1 | 453 | 76 |
| 0 | 69 | 73 |

Example 3
Isolation and Purification of Poly(A)-containing Vaccinia Virus mRNA
(1) Preparation of Poly(A)-containing Vaccinia Virus mRNA The preparation was carried out as described in Example 2-(2) except that the concentration of uridine triphosphate contained in the solution added to the pellet obtained by centrifugation after treating Vaccinia virus with NP40 was 0.5 mM and 50 μCi of α-$^{32}$P-uridine triphosphate were added to the solution.

(2) Isolation and Purification of mRNA From Impurities

10 μl (0.5% (w/v)] of a suspension of hybridization carrier prepared as described in Example 2-(1) were added a microcentrifuge tube, followed by 50 μl of 10 mM Tris-HCl buffer (pH 7.5) containing 0.5 M sodium chloride, 0.1% (w/v) sodium dodecylsulfate and 1 mM EDTA, 50 μg of bovine serum albumin, 30 μg of ribosomal RNA, 30 μg of transfer RNA and 300 ng of the poly(A) sequence-containing mRNA prepared in (1). The mixture was incubated at 37° C. for 10 minutes. There after, the incubated product was centrifuged at 10,000 rpm for 5 minutes to separate the mixture into a supernatant and a solid fraction. The radioactivity in both fractions was measured by Cerenkov's counting method. The hybridization efficiency was calculated at 94.7% according to the following equation:

$$\frac{\text{Count Number of Hybridization Carrier}}{\text{(Count Number of Supernatant)} + \text{(Count Number of Hybridization Carrier)}}$$

10 μl of 10 mM Tris-HCl buffer (pH 7.5) containing 0.1% (w/v) sodium dodecylsulfate and 1 mM EDTA were added to the hybridization carrier prepared in the above (1). followed by heating at 65° C. for 5 minutes. The resulting product was then centrifuged at 10,000 rpm for 5 minutes to separate the same into the supernatant and the hybridization carrier, followed by measuring each radioactivity according to Cerenkov's counting method. The recovery was calculated at 91.6% according to the following equation:

$$\frac{\text{Count Number of Supernatant}}{\text{(Count Number of Supernatant)} + \text{(Count Number of Hybridization Carrier)}}$$

Example 4
Isolation and Purification of Globin mRNA
(1) Isolation and Purification of Globin mRNA 200 μl of a 0.5% (w/v) suspension of hybridization carrier prepared as described in Example 2-(1) were added to a 1.5-ml microcentrifuge tube and centrifuged at 15.000 rpm for 5 minutes. The supernatant was discarded.

100 μl of binding buffer having the same composition as in Example 1-(3) and 20 μl of a sterile aqueous solution containing 50 μg/ml of globin mRNA (hereinafter referred to as "Sample O"; Bethesda Research, Inc.) were added to the centrifuge tube, and mixed thoroughly. The mixture was then incubated at 37° C. for 10 minutes. Thereafter, the incubated mixture was centrifuged at 15,000 rpm for 5 minutes to collect the supernatant (hereinafter referred to as "Sample U"). To the precipitated hybridization carrier were added 100 μl of elution buffer [10 mM Tris-HCl buffer (pH 7.5). 0.1% (w/v) sodium dodecylsulfate and 1 mM EDTA] to redisperse the hybridization carrier therein. The redispersed hybridization carrier was heated at 65° C. for 5 minutes, and then centrifuged at 4° C. and 15,000 rpm for 5 minutes. The supernatant (hereinafter referred to as "Sample B") was collected.

Samples U and B were separately subjected to ethanol precipitation to recover the nucleic acids contained in each sample.

(2) Synthesis of Globin

To confirm that the globin mRNA obtained in (1) above had a complete structure, Sample U, B or O was treated with a translation kit (du Pont) to make the globin mRNA in each sample synthesize globin protein. The synthesis was carried out as described by the manual provided with the kit.

After synthesis of the globin proteins was complete, each reaction solution was subjected to electrophoresis in 15% (w/v) SDS-polyacrylamide gels. The gels were dried and subjected to autoradiography. For comparison, a blank not containing mRNA was also subjected to autoradiography. A sketch of the obtained autoradiograms is given in FIG. 1.

The autoradiograms confirmed that the globin mRNA isolated in Sample B did not lose the function of mRNA of Sample O and that no globin mRNA remained in Sample U.

(3) Synthesis of Globin Complementary DNA (cDNA)

Samples B and O described in (1) above were treated with a cDNA synthesis kit (Amersham Int., Ltd.) to synthesize the complementary DNAs.

Figure 2:
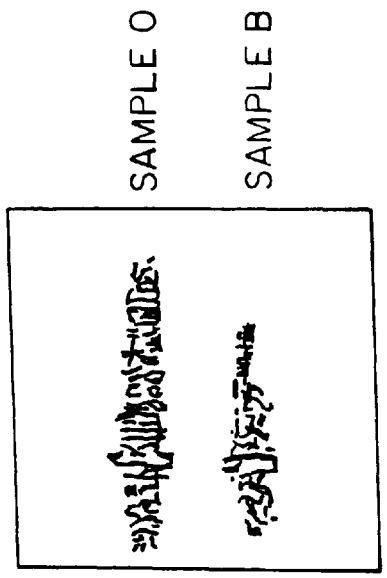

This synthesis was carried out using reagents provided with the kit following the manufacture's instructions, except that 50 μCi of α-$^{32}$P-deoxycytidine triphosphate were used. After completion of the synthetic reaction, 5 μl of the reaction solution were subjected to electrophoresis using 1% (w/v) agarose gel. The gel was dried and subjected to autoradiography. A sketch of the autoradiograms obtained is given in FIG. 2.

These autoradiograms show that the purity of the globin mRNA of Sample B was higher than that of Sample O.

Many modifications and variations of this invention may be made without departing from its spirit and scope, as will become apparent to those skilled in the art. The specific embodiments described herein are offered by way of example only, and the invention is limited only by the terms of the appended claims.

What is claimed is:

1. A hybridization carrier, comprising a single-stranded polynucleotide having the formula:

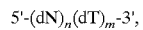

5'-(dN)$_n$(dT)$_m$-3', wherein N represents adenine, guanine or cytosine; T represents thymine; n is an integer of 2 or larger; and m is an integer of 5 or larger;

said polynucleotide being immobilized by an amide bond on a surface of an organic polymer particle having a diameter of from about 0.05 μm to about 5 μm;

said polynucleotide being immobilized at the site of a nucleotide sequence consisting of 2 or more nucleotides each containing a primary amino residue therein; and said amide bond having been formed between said primary amino residue and a carboxyl residue on the surface of said organic polymer particle;

said surface of the polymer particle being non-porous or having pores no larger than 100 Å.

2. The hybridization carrier of claim 1, wherein the diameter of the particle is from about 0.2 to about 4 $\mu$m.

3. The hybridization carrier of claim 1, wherein said organic polymer particle is made of a water-insoluble organic polymer obtained by polymerizing one or more vinyl aromatic compounds, esters or amides of $\alpha,\beta$-unsaturated carboxylic acids $\alpha,\beta$-unsaturated nitrile compounds, halogenic vinyl compounds, conjugated-diene compounds or lower fatty acid vinyl ester compounds.

4. The hybridization carrier of claim 1, wherein said organic polymer particle further comprises magnetic powder.

5. The hybridization carrier of claim 1, wherein said organic polymer particle is non-swelling.

6. The hybridization carrier of claim 1, wherein said polynucleotide is immobilized at the site of a nucleotide sequence consisting of 2 to 15 nucleotides containing primary amino residues.

7. The hybridization carrier of claim 1, wherein said 2 or more nucleotides containing a primary amino residue are selected from the group consisting of deoxyadenylic acid (dA), deoxycytidylic acid (dC), and deoxyguanylic acid (dG).

8. The hybridization carrier of claim 7, wherein said 2 or more nucleotides containing a primary amino residue is selected from the group consisting of (dA) and (dC).

9. The hybridization carrier of claim 7, wherein said 2 or more nucleotides are all (dA).

10. The hybridization carrier of claim 9, wherein said 2 or more nucleotides are all (dC).

11. The hybridization carrier of claim 1, wherein a density of carboxyl residues on a surface of the organic polymer particle is at least 1 per nm$^2$ of surface area.

12. The hybridization carrier of claim 11, wherein the density is 3 or more per nm$^2$ of surface area.

13. The hybridization carrier of claim 12, wherein the density is 5 or more per nm$^2$ of surface area.

14. The hybridization carrier of claim 1, wherein said single-stranded polynucleotide has the formula:

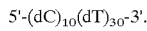
5'-(dC)$_{10}$(dT)$_{30}$-3'.

15. A method for isolating mRNA from a sample, comprising:

(a) providing a hybridization carrier, comprising a single-stranded polynucleotide having the formula:

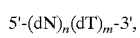
5'-(dN)$_n$(dT)$_m$-3', wherein N represents adenine, guanine or cytosine; T represents thymine; n is an integer of 2 or larger; and m is an integer of 5 or larger;

said polynucleotide being immobilized by an amide bond on a surface of an organic polymer particle having a diameter of from about 0.05 $\mu$m to about 5 $\mu$m;

said polynucleotide being immobilized at the site of a nucleotide sequence consisting of 2 or more nucleotides which each contain a primary amino residue in said polynucleotide; and said amide bond having been formed between said primary amino residue and a carboxyl residue on the surface of said organic polymer particle;

said surface of the polymer particle being non-porous or having pores no larger than 100 Å;

(b) contacting a sample containing mRNA with the hybridization carrier under conditions in which specific hybridization occurs between an oligo (dT) sequence of the carrier and poly (A) sequences in the mRNA to produce a carrier-mRNA hybrid;

(c) washing the hybrid to remove unbound materials from the sample;

(d) treating the washed hybrid to cause the mRNA to dissociate from the hybrid; and (e) separating the carrier from the dissociated mRNA.

16. The method of claim 15, wherein the mRNA is dissociated from the washed hybrid by heat treatment.

17. The method of claim 15, wherein mRNA is dissociated from the washed hybrid by a chemical agent selected from the group consisting of alkali, formamide or urea.

18. A method for detecting a specific mRNA in a sample, comprising:

(a) providing a hybridization carrier comprising a single-stranded polynucleotide having the formula;

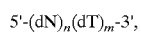
5'-(dN)$_n$(dT)$_m$-3', wherein N represents adenine, guanine or cytosine; T represents thymine; n is an integer of 2 or larger; and m is an integer of 5 or larger, said polynucleotide being immobilized by an amide bond on a surface of an organic polymer particle having a diameter of from about 0.05 $\mu$m to about 5 $\mu$m;

said polynucleotide being immobilized at the site of a nucleotide sequence consisting of 2 or more nucleotides which each contain a primary amino residue in said polynucleotide; and said amide bond having been formed between said primary amino residue and a carboxyl residue on the surface of said organic polymer particle;

said surface of the polymer particle being non-porous or having pores no larger than 100 Å;

(b) contacting a sample suspected to contain a specific mRNA with the hybridization carrier and with a labeled nucleic acid probe, which probe has a nucleotide sequence that is complementary to the specific mRNA at a point other than the poly (A) sequences in the mRNA, under conditions in which specific hybridization occurs to form a hybrid between the carrier polynucleotide, the specific mRNA and the labeled probe;

(c) washing the hybrid to remove unbound sample materials and unbound labeled probe; and (d) measuring the amount of labeled probe associated with the washed hybrid; thereby detecting the specific mRNA in the sample.

19. A method for detecting a specific mRNA in a sample, comprising:

(a) providing a hybridization carrier comprising a single-stranded polynucleotide having the formula;

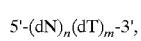
5'-(dN)$_n$(dT)$_m$-3', wherein N represents adenine, guanine or cytosine; T represents thymine; n is an integer of 2 or larger; and m is an integer of 5 or larger;

said polynucleotide being immobilized by an amide bond on a surface of an organic polymer particle having a diameter of from about 0.05 μm to about 5 μm;

said polynucleotide being immobilized at the site of a nucleotide sequence consisting of 2 or more nucleotides which each contain a primary amino residue in said polynucleotide; and said amide bond having been formed between said primary amino residue and a carboxyl residue on the surface of said organic polymer particle;

said surface of the polymer particle being non-porous or having pores no larger than 100 Å;

(b) contacting a sample suspected to contain a specific mRNA with the hybridization carrier and with a labeled nucleic acid probe, which probe has a poly (A) sequence homologous to that of the specific mRNA, under conditions in which specific hybridization occurs to form a hybrid between the carrier and the specific mRNA or the labeled probe, whereby increasing amounts of the specific mRNA in the sample will produce decreasing amounts of the labeled probe in the hybrid;

(c) washing the hybrid to remove unbound sample materials and unbound labeled probe; and (d) measuring the amount of labeled probe associated with the washed hybrid, thereby detecting the specific mRNA in the sample.

20. A method for producing cDNA from a specific mRNA in a sample, comprising:

(a) providing a hybridization carrier comprising a single-stranded polynucleotide having a nucleotide sequence complementary to a subsequence of a specific mRNA, said polynucleotide being immobilized by an amide bond on a surface of an organic polymer particle having a diameter of from about 0.05 μm to about 5 μm;

said polynucleotide being immobilized at the site of a nucleotide sequence consisting of 2 or more nucleotides which each contain a primary amino residue in said polynucleotide; and said amide bond having been formed between said primary amino residue and a carboxyl residue on the surface of said organic polymer particle;

said surface of the polymer particle being non-porous or having pores no larger than 100 Å

(b) contacting a sample containing the specific mRNA with the hybridization carrier under conditions in which specific hybridization occurs to form a hybrid between the carrier polynucleotide and the specific mRNA;

(c) washing the hybrid to remove unbound sample materials;

(d) synthesizing a first complementary DNA strand with reverse transcriptase, using the specific mRNA as a template and the immobilized polynucleotide as a primer;

(e) synthesizing a second complementary DNA strand with DNA polymerase, using the first complementary DNA strand as a template; and (f) separating the cDNA from the organic polymer particle, thereby producing cDNA from the specific mRNA.

21. The method of claim 20, wherein the immobilized polynucleotide contains a restriction endonuclease recognition site and the polynucleotide is cleaved from the particle by a corresponding endonuclease following the synthesis of the second complementary DNA strand.

* * * * *